US011361415B2

United States Patent
Prevrhal et al.

(10) Patent No.: US 11,361,415 B2
(45) Date of Patent: Jun. 14, 2022

(54) MATERIAL-SELECTIVE ADAPTIVE BLENDING OF VOLUMEIRIC IMAGE DATA

(71) Applicant: KONINKLIJKE PHILIPS N.V., Eindhoven (NL)

(72) Inventors: Sven Prevrhal, Hamburg (DE); Manindranath Vembar, Twinsburg, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 232 days.

(21) Appl. No.: 16/753,825

(22) PCT Filed: Sep. 26, 2018

(86) PCT No.: PCT/EP2018/076055
§ 371 (c)(1),
(2) Date: Apr. 6, 2020

(87) PCT Pub. No.: WO2019/072554
PCT Pub. Date: Apr. 18, 2019

(65) Prior Publication Data
US 2021/0407056 A1     Dec. 30, 2021

Related U.S. Application Data

(60) Provisional application No. 62/569,756, filed on Oct. 9, 2017.

(51) Int. Cl.
*G06T 5/00* (2006.01)
*G06T 5/50* (2006.01)
*A61B 6/03* (2006.01)

(52) U.S. Cl.
CPC ............... *G06T 5/50* (2013.01); *A61B 6/032* (2013.01); *G06T 5/002* (2013.01);
(Continued)

(58) Field of Classification Search
CPC . G06T 5/50; G06T 5/002; G06T 2207/10081; G06T 2207/20012;
(Continued)

(56) References Cited

U.S. PATENT DOCUMENTS 7,968,853 B2    6/2011  Altman
8,442,184 B2    5/2013  Forthmann
(Continued)

FOREIGN PATENT DOCUMENTS

WO    WO2007029129 A2    3/2007
WO    WO2009072056 A2    6/2009
(Continued)

OTHER PUBLICATIONS

PCT International Search Report, International application No. PCT/EP2018/076055, dated Jan. 3, 2019.

*Primary Examiner* — Jose L Couso
(74) *Attorney, Agent, or Firm* — Larry Liberchuk

(57) ABSTRACT

An imaging system (500) includes a data acquisition system (515) configured to produce projection data and at least one memory device with reconstruction algorithms (518) and at least one blending algorithm (524). The imaging system further includes a reconstructor (516) configured to reconstruct the projection data with the reconstruction algorithms and generate at least first spectral volumetric image data corresponding to a first basis material content and second spectral volumetric image data corresponding to a second basis material content, and blend the first spectral volumetric image data and the second spectral volumetric image data with the at least one blending algorithm to produce blended volumetric image data.

20 Claims, 4 Drawing Sheets

(52) U.S. Cl.
CPC ............... *G06T 2207/10081* (2013.01); *G06T 2207/20012* (2013.01); *G06T 2207/20221* (2013.01)

(58) Field of Classification Search
CPC ... G06T 2207/20221; G06T 5/00; G06T 5/20; G06T 11/00; G06T 11/06; G06T 11/005; G06T 11/008; G06T 2207/30004; G06T 2207/30008; G06T 2207/30101; G06T 2211/424; G06T 2211/416; G06T 2211/421; A61B 6/032; A61B 6/03; A61B 6/481; A61B 6/507; A61B 6/5217; A61B 6/5205; A61B 6/503; A61B 6/541; A61B 6/027; A61B 6/5229; A61B 6/5258; A61B 5/055; A61B 5/0295; A61B 5/742; A61B 2090/374; A61B 2090/3762; A61B 2576/02; G01N 23/04; G01N 23/046; G01N 2223/419; G06K 9/40; G06K 9/36; G01V 5/005
See application file for complete search history.

(56) References Cited

U.S. PATENT DOCUMENTS

| | | | |
|---|---|---|---|
| 9,271,688 B2* | 3/2016 | Das | A61B 6/481 |
| 9,830,685 B2* | 11/2017 | Dennerlein | G06T 5/001 |
| 2004/0109532 A1 | 6/2004 | Ford | |
| 2008/0037699 A1* | 2/2008 | Krauss | A61B 6/032 378/4 |
| 2009/0052727 A1* | 2/2009 | Eusemann | G06T 11/00 382/100 |
| 2014/0133622 A1* | 5/2014 | Yin | A61B 6/5205 378/8 |
| 2016/0012615 A1* | 1/2016 | Gao | A61B 6/032 382/131 |
| 2017/0014069 A1 | 1/2017 | Carmi | |

FOREIGN PATENT DOCUMENTS

| | | |
|---|---|---|
| WO | WO2013011418 A2 | 1/2013 |
| WO | WO2016035048 A1 | 3/2016 |

* cited by examiner

MATERIAL-SELECTIVE ADAPTIVE BLENDING OF VOLUMEIRIC IMAGE DATA

FIELD OF THE INVENTION

The following generally relates to imaging and more particularly to material-selective adaptive blending of volumetric image data and is described with particular application to computed tomography (CT), including spectral and non-spectral CT.

BACKGROUND OF THE INVENTION

A computed tomography (CT) scanner generally includes an x-ray tube mounted on a rotatable gantry opposite one or more rows of detectors. The x-ray tube rotates around an examination region located between the x-ray tube and the one or more rows of detectors and emits radiation that traverses the examination region and a subject and/or object disposed in the examination region. The one or more rows of detectors detect radiation that traverses the examination region and generate a signal (projection data) indicative of the examination region and the subject and/or object disposed therein.

The projection data is reconstructed to generate volumetric image data by means of a computer, which can be used to generate one or more images. The resulting image(s) includes pixels that are represented in terms of gray scale values corresponding to relative radiodensity. Such information reflects the attenuation characteristics of the scanned subject and/or object, and generally shows structure such as anatomical structures within a patient, physical structures within an inanimate object, and the like. These images are dependent on the X-ray source and properties of the photon detectors.

The radiation imparted on the examined object or body part also includes spectral information since the absorption of the radiation by the subject and/or object is dependent on the energy of the photons traversing there through. Such spectral information provides additional information such as information indicative of elemental or material composition (e.g., atomic number) of tissue and/or a material of the subject and/or object. However, the projection data does not reflect the spectral characteristics as the data it represents is proportional to the energy fluence integrated over the energy spectrum.

A CT scanner configured for spectral (multi-energy) imaging leverages the spectral characteristics. For example, with a dual energy system, basis images reflecting intrinsic properties (tissue composition) of a material being imaged (e.g., the photoelectric effect (PE) and Compton scattering (CS) behavior of each component of the tissue, etc.) can be generated. Although such images allow discrimination of materials based on energy attenuation characteristics, in some instances there is a trade-off between image quality improvement and degradation.

For example, in non-spectral CT angiographic imaging of arterial narrowing by calcified arterial plaque, the calcium can cause "blooming" artifact in which a calcification appears larger than its actual size. Blooming artifact is reduced at higher X-ray energies. However, CT value difference ("contrast") between the iodinated contrast media and surrounding tissue is reduced, and this contrast difference has been utilized to segment the arteries for further analysis, e.g., with computed tomography fractional flow reserve (CT-FFR) simulations, which have been used to determine, e.g., whether the lesion is flow-limiting and any intervention is warranted, etc.

FIGS. 1-4 illustrate "blooming" artifact. FIG. 1 shows a calcification 102 and a vessel segmentation 104 in a lower energy multi-planar reformatted (MPR) image, and FIG. 2 shows a calcification 202 and a vessel segmentation 204 in a higher energy MPR image. FIGS. 3A and 3B are magnified views of the calcifications 102 and 202 and sub-portions of the segmentations 104 and 204. The enlarged (due to "blooming") calcification 102 in FIG. 3A has a height 302, which is greater than a height 304 of the calcification 102 in the higher energy image in FIG. 3B. As a consequence, a size of the lumen of the vessel 306 in FIG. 3A is smaller than a corresponding size of the lumen of the vessel 308 in the higher energy image in FIG. 3B, thereby indicating a greater narrowing, 306 in FIG. 3A, compared to 308 in FIG. 3B.

Although the stenosis in the higher energy image of FIG. 3B more accurately reflects the actual stenosis geometry since the "blooming" artifact is reduced, the decreased contrast between the iodinated contrast media and surrounding tissue may result in a less accurate vessel segmentation. An example is shown in FIGS. 4A and 4B, which are magnified views of sub-portions of the segmentations 104 and 204. From FIGS. 4A and 4B, due at least to the reduced contrast, the vessel wall in the higher energy image of FIG. 4B is more irregular than the vessel wall in FIG. 4A.

SUMMARY OF THE INVENTION

Aspects described herein address the above-referenced problems and others.

In one aspect, an imaging system includes a data acquisition system configured to produce projection data. The imaging system further includes at least one memory device. The memory at least includes reconstruction algorithms and at least one blending algorithm. The imaging system further includes a reconstructor configured to reconstruct the projection data with the reconstruction algorithms and generate at least first spectral volumetric image data corresponding to a first basis material content and second spectral volumetric image data corresponding to a second basis material content, and blend the first spectral volumetric image data and the second spectral volumetric image data with the at least one blending algorithm to produce blended volumetric image data.

In another aspect, a method includes performing a contrast enhanced scan, which produces projection data and reconstructing the projection data to produce non-spectral volumetric image data. The method further includes reconstructing the projection data to produce first spectral volumetric image data for a first basis material, and reconstructing the projection data to produce second spectral volumetric image data for a second basis material. The method further includes blending at least two of the non-spectral volumetric image data, the first spectral volumetric image data, and the second spectral volumetric image data, producing blended volumetric image data.

In another aspect, a computer readable medium is encoded with computer executable instructions, which, when executed by a processor of a computer, cause the processor to: receive projection data generated from a contrast enhanced scan, reconstruct the projection data to produce non-spectral volumetric image data, reconstruct the projection data to produce first spectral volumetric image data for a first basis material, reconstruct the projection data to produce second spectral volumetric image data for a second basis material, and blend at least two of the non-spectral volumetric image data, the first spectral volumetric image data, and the second spectral volumetric image data, producing blended volumetric image data.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
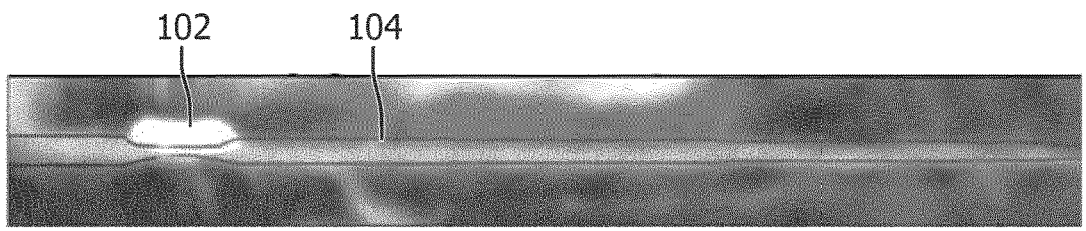
FIG. 1 shows a prior art example of a lower energy contrast enhanced image with calcium, blooming artifact, and a segmented vessel.
Figure 2:
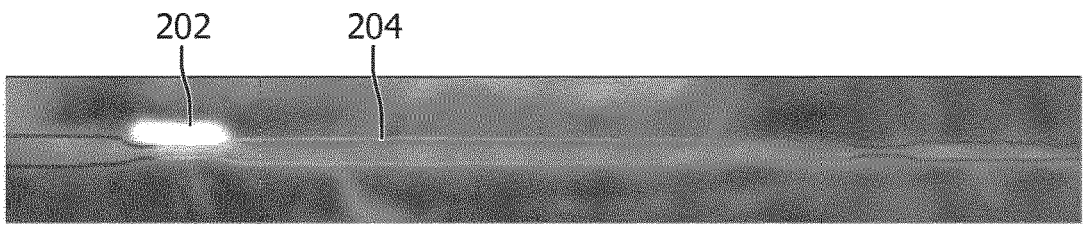
FIG. 2 shows a prior art example of a higher energy contrast enhanced image with calcium, less blooming artifact than FIG. 1, and a segmented vessel.
Figure 3A:
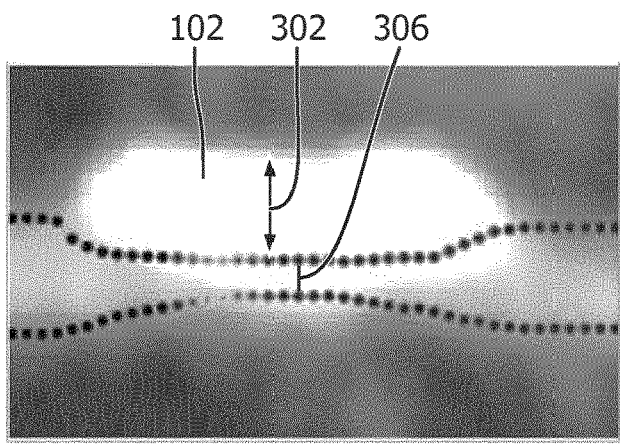
FIG. 3A shows a magnified view of the blooming artifact of FIG. 1.
Figure 4A:
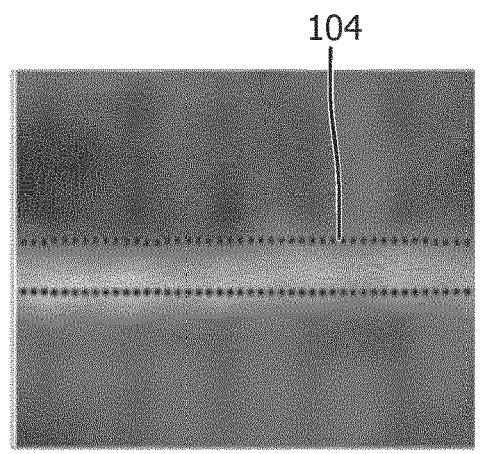
FIG. 4A shows a magnified view of the segmentation of the normal portion of the vessel in FIG. 1.
Figure 3B:
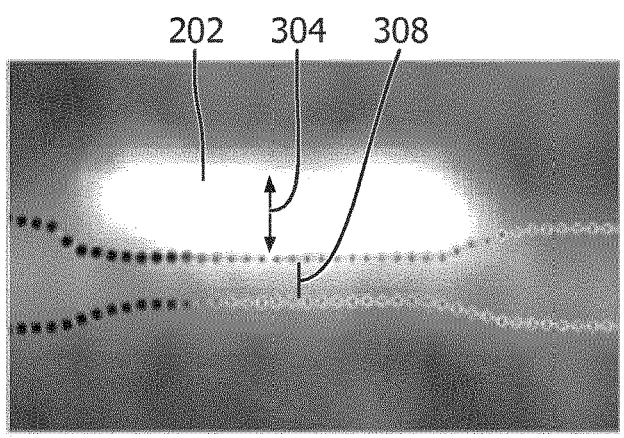
FIG. 3B shows a magnified view of the reduced blooming artifact of FIG. 2.
Figure 4B:
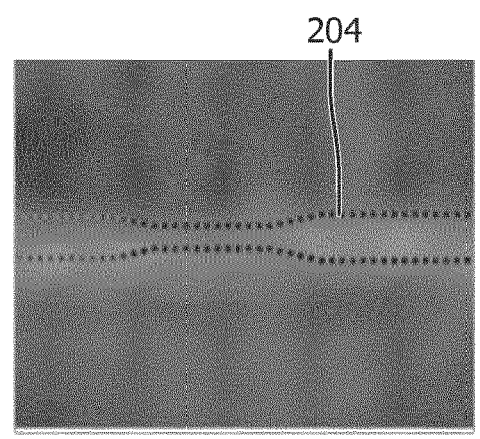
FIG. 4B shows a magnified view of the segmentation of the normal portion of the vessel in FIG. 2.
Figure 5:
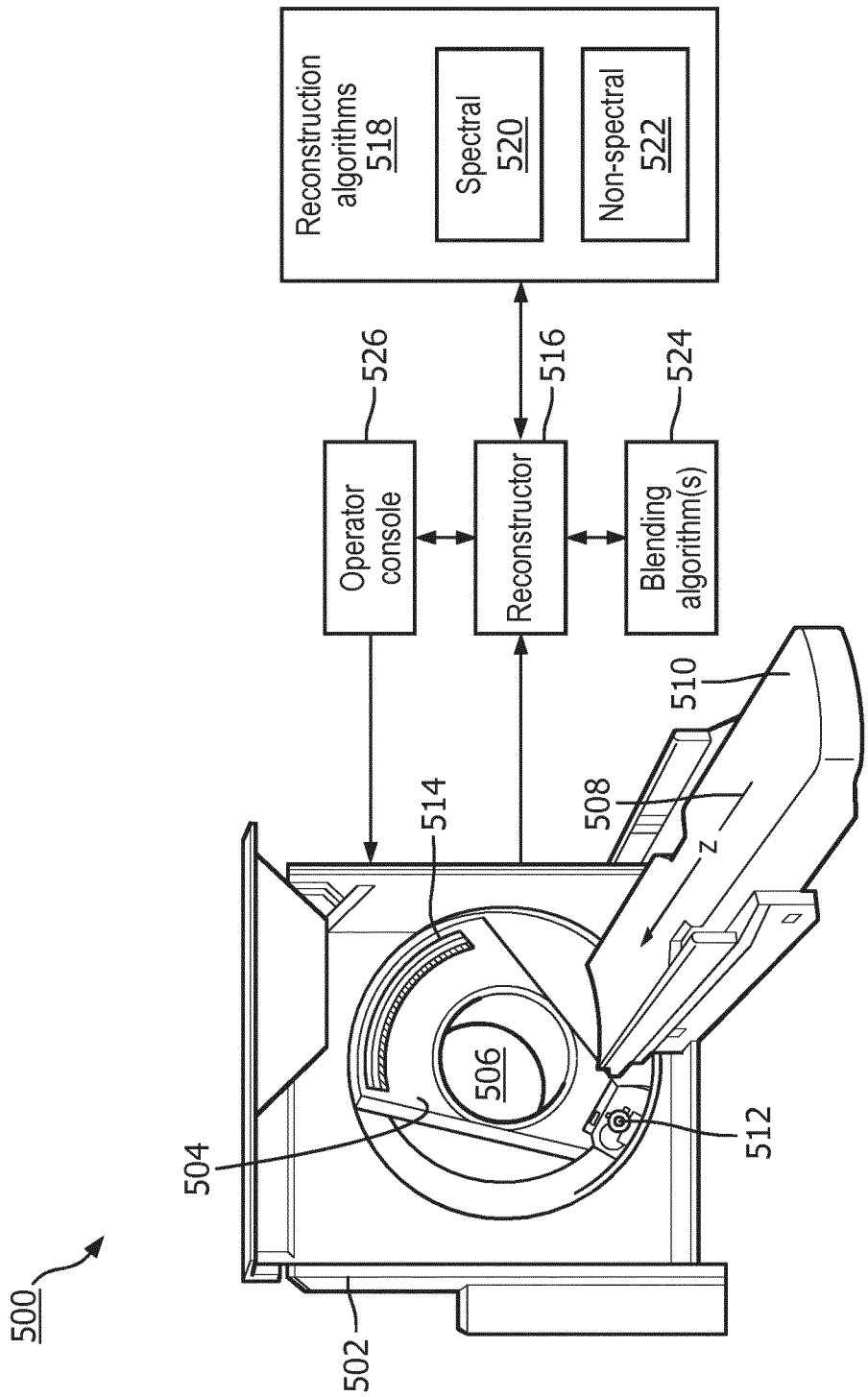
FIG. 5 schematically illustrates an imaging system with a reconstructor, a reconstruction algorithm, and a blending algorithm.

FIG. 5 schematically illustrates an imaging system 500 such as a computed tomography (CT) scanner. The imaging system 500 includes a generally stationary gantry 502 and a rotating gantry 504. The rotating portion of the gantry 504 is supported by the stationary part 502 and rotates around an examination region 106 about a longitudinal or z-axis 508. A subject support 510, such as a couch, supports an object or subject in the examination region. The subject support 510 is movable in coordination with performing an imaging procedure so as to guide the subject or object with respect to the examination region 506 for loading, scanning, and/or unloading the subject or object.

A radiation source 512, such as an x-ray tube, is supported by the rotating gantry 504. The radiation source 512 rotates with the rotating gantry 504 and emits X-ray radiation that traverses the examination region 506. In the illustrated embodiment, the radiation source 512 is a single x-ray tube configured to emit broadband radiation for a single selected peak emission voltage (kVp) of interest (i.e. the energy spectrum at that kVp). In another instance, the radiation source 512 is configured to switch between at least two different emission voltages (e.g., 70 keV, 100 keV, etc.) during scanning In yet another instance, the radiation source 512 includes two or more x-ray tubes angular offset on the rotating gantry 504 with each configured to emit radiation with a different mean energy spectrum. U.S. Pat. No. 8,442,184 B2 describes a system with kVp switching and multiple x-ray tubes, and is incorporated herein by reference in its entirety.

A radiation spectrum sensitive detector array 514 subtends an angular arc opposite the radiation source 512 across the examination region 506. The detector array 514 includes one or more rows of detectors that arranged with respect to each other along the z-axis 508 direction and detects radiation traversing the examination region 506. In the illustrated embodiment, the detector array 214 includes an energy-resolving detector such as a multi-layer scintillator/photosensor detector (e.g., U.S. Pat. No. 7,968,853 B2, which is incorporated herein by reference in its entirety) and/or a photon counting (direct conversion) detector (e.g., WO2009072056A2, which is incorporated herein by reference in its entirety). With an energy-resolving detector, the radiation source 512 includes the broadband, kVp switching and/or multiple X-ray tube radiation source 512. In another instance, the detector array 514 includes a non-energy-resolving detector, and the radiation source 512 includes the kVp switching and/or the multiple X-ray tube radiation source 512. The detector array 514 generates projection data indicative of the different energies.

The radiation source 512 and the radiation spectrum sensitive detector array 514 can be collectively referred to as part of a data acquisition (515).

A reconstructor 516 reconstructs this same set of projection data with multiple different reconstruction algorithms 518, including a spectral reconstruction algorithm(s) 520 and a non-spectral reconstruction algorithm(s) 522. The non-spectral reconstruction algorithm(s) 522 produces conventional broadband (non-spectral) volumetric image data, e.g., by combing the spectral projection data and reconstructing the combined volumetric image data. The spectral reconstruction algorithm(s) 520 produces basis volumetric image data, e.g., first basis volumetric image data, second basis volumetric image data, . . . , Nth basis volumetric image data. For example, for dual energy, the reconstructor 516 can generate photoelectric effect and Compton scatter volumetric image data sets, mono-energetic/monochrome volumetric image data sets (e.g., 70 keV and 100 keV), calcium and iodine volumetric image data sets, bone and soft tissue volumetric image data sets, etc. Other data sets include effective Z (atomic number), k-edge, etc. volumetric image data sets.

As described in greater detail below, the reconstructor 516 is configured to blend volumetric image data together to produce blended volumetric image data based on a blending algorithm(s) 524. For example, the reconstructor 516 can selectively combine different regions of two or more virtual mono-energetic and/or material-selective volumetric image data sets. This can mitigate instances where a specific energy improves a visual characteristic while degrading another visual characteristic. The reconstructor 516 includes at least one processor (e.g., a central processing unit or CPU, a microprocessor, etc.) and a computer readable storage medium (which excludes transitory medium), such as physical memory, a memory device, and/or other non-transitory memory. The computer readable storage medium stores computer readable instructions and data (e.g., the algorithms 518 and/or 524). The at least one processor is configured to execute the instructions. The at least one processor can also execute instructions carried by transitory medium such as a signal, a carrier wave, and/or other transitory medium.

An operator console 526 allows an operator to control an operation of the system 500. This includes selecting an imaging acquisition protocol (e.g., multi-energy), selecting a reconstruction algorithm (e.g., multi-energy), selecting a blending algorithm, invoking scanning, invoking a visualization software application, interacting with an executing visualization software application, etc. The imaging acquisition protocol can alternatively be automatically selected, e.g., via artificial intelligence and/or otherwise. The operator console 526 includes an output device(s) such as a display monitor, a filmer, etc., and an input device(s) such as a mouse, keyboard, etc. The reconstruction algorithm(s) 518 and/or the blending algorithm(s) 524 can be stored in computer readable storage medium of the operator console 526, the reconstructor 516, a separate computer workstation, located in a remote location, and/or other storage medium.

As briefly discussed above, the reconstructor 516, in one embodiment, is configured to selectively blend different regions of different energy volumetric image data based on the blending algorithm(s) 524 to produce blended volumetric image data. For example, in one instance, the reconstructor 516 employs a reconstruction algorithm that produces non-spectral volumetric image data, first spectral volumetric image data for a first material of interest, and second spectral volumetric image data for a second material of interest, all from a sub-set of or all of the same projection data from the same scan.

For volumetric image data, the reconstructor 516 creates maps that identify the voxels that contain the material of interest. For example, for the first spectral volumetric image data, a first map is produced which denotes, on a voxel basis, which voxels contain mostly the first material. For instance, voxels with mostly the first material can each be given a value of one (1) in the map and the other voxels can each be given a value of zero (0) in the map. The same is done for the volumetric image data for the other material(s) of interest. These maps are then used for blending the volumetric image data.

For instance, for voxels containing mostly the first material, as determined by the corresponding first map, the voxel values of the non-spectral volumetric image data are down-weighted and the voxel values of the first spectral volumetric image data are up-weighted, and the weighted voxels values are combined (e.g., summed and normalized, averaged, etc.). The weighting can take on values from zero (0) to one (1). For example, the up-weighting and down-weighting can be 1.0 and 0.0, 0.9 and 0.01, 0.8 and 0.02, . . . , 0.5 and 0.5, . . . , 0.1 and 0.9, and/or other weighting.

Likewise, for voxels containing mostly the second material, as determined by the corresponding second map, the voxel values of the non-spectral volumetric image data are down-weighted and the voxel values of the second spectral volumetric image data are up-weighted, and the weighted voxels values are combined. Voxels in between can be blended for a smooth transition. This may include using a smoothing function such as a sigmoid, hyperbolic tangent, and/or other smoothing function. In general, the smoothing function will be a monotonically increasing (or decreasing) function.

For voxels with neither material, the voxel values of the non-spectral volumetric image data are used, or the weighting for the voxel values of the non-spectral volumetric image data is one and the weighting for the voxel values of the spectral volumetric image data is zero. Likewise, values of voxels between these voxels and the voxels weighted for the first or second materials are blended for a smooth transition there between.

In one instance, this location-specific adaptation of blending properties allows optimization of image contrast depending on its materials content.

Where the selected protocol is an angiographic protocol for a contrast enhanced scan that produces volumetric image data to be evaluated for arterial narrowing by calcified arterial plaque, the first and second materials may respectively be calcium and iodine. In this instance, the reconstructor 516 reconstructs calcium basis, higher energy (e.g., 100 keV), and/or other spectral volumetric image data that emphasizes calcium, and iodine basis, lower energy (e.g., 70 keV), and/or other spectral volumetric image data that emphasizes iodine. In this instance, the first and second maps indicate mostly calcium and mostly iodine voxels.

For voxels containing mostly calcium, the voxel values of the non-spectral volumetric image data are down-weighted and the voxel values of the calcium spectral volumetric image data are up-weighted. For voxels containing mostly iodine, the voxel values of the non-spectral volumetric image data are down-weighted and the voxel values of the iodine spectral volumetric image data are up-weighted. Values of voxels containing neither are determined from the non-spectral volumetric image data. Values of voxels between calcium and iodine, between calcium and non-spectral, and between iodine and non-spectral are blended for a smooth transition there between.

In this example, the blended volumetric image data reduces blooming artifact with the higher energy image data while maintaining CT value differences between iodinated contrast media and surrounding tissue with the non-spectral (or lower energy) image data. That is, in the blended volumetric image data, the calcium spectral volumetric image data contributes to a greater degree (relate to other volumetric image data) to the voxels representing calcium, the iodine spectral volumetric image data contributes to a greater (relate to other volumetric image data) degree to the voxels representing iodine, and the remaining voxels either represents other (e.g., the non-spectral) volumetric image data or a transition between and/or to the voxels with the adjusted values.

This approach is well-suited for applications which automatically and/or manually identify stenosis and segment vessels. One such application is fractional flow reserve (FFR) simulation, such as CT-FFR. The identification of the stenosis as well as the diameter of the walls of a vessel before and after the stenosis can be more accurately determined, in one instance, from the resulting blended volumetric image data relative to using non-spectral volumetric image data, the calcium volumetric image data, the iodine volumetric image data, or other spectral volumetric image data. In cardiac applications, such blending can be utilized with data for one or more cardiac phases.

The foregoing provides a specific example for calcium and iodine. Other materials of interest may include uric acid, gold, bone, iodine, metal, and/or other materials.

In general, the reconstructor 516 can produce and blend volumetric image data for any two (or more) basis materials of interest to produce a single blended volumetric image data set that optimizes image quality for all (or a predetermined sub-set of) materials contained in it, where the individual set of volumetric image data may emphasize one material to a detriment of another material.

In the above, the non-spectral volumetric image data and spectral volumetric image data are blended. In a variation, only spectral volumetric image data sets are blended. In another variation, only one set of the spectral volumetric image data is blended with the non-spectral volumetric image data. For example, in one instance only the calcium spectral volumetric image data is blended with the non-spectral volumetric image data to reduce blooming while maintaining the iodine and soft tissue contrast difference from the non-spectral volumetric image data.

Figure 6:
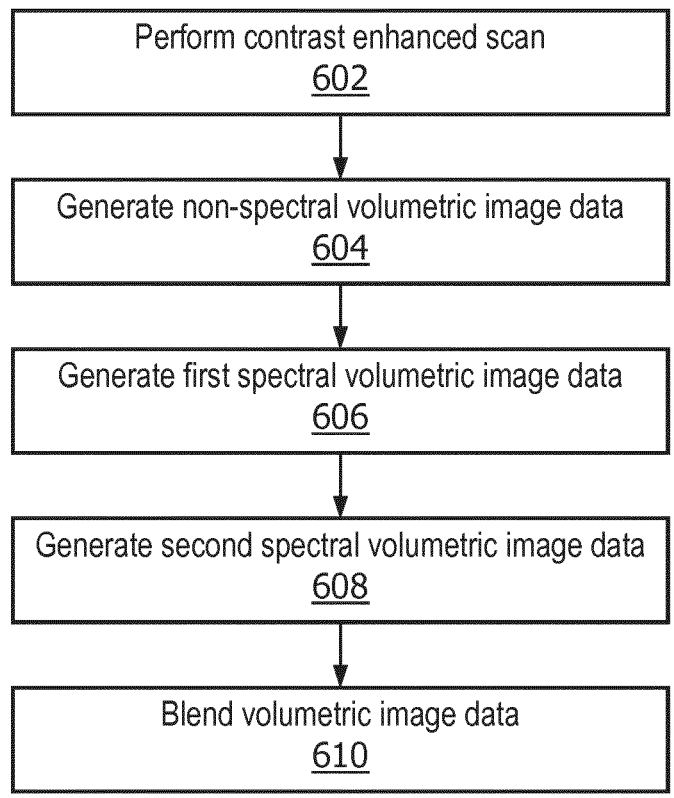
FIG. 6 illustrates an example method in accordance with an embodiment herein.

FIG. 6 illustrates an example method in accordance with an embodiment(s) described herein.

It is to be appreciated that the ordering of the acts in the method is not limiting. As such, other orderings are contemplated herein. In addition, one or more acts may be omitted and/or one or more additional acts may be included.

At 602, a contrast enhanced scan is performed.

At 604, non-spectral volumetric image data is reconstructed.

At 606, first spectral volumetric image data emphasizing a first material of interest is reconstructed.

At 608, second spectral volumetric image data emphasizing a second material of interest is reconstructed.

At 610, the non-spectral volumetric image data, the first spectral volumetric image data and/or the second spectral volumetric image data are blended together to produce blended volumetric image data, as described herein and/or otherwise.

Figure 7:
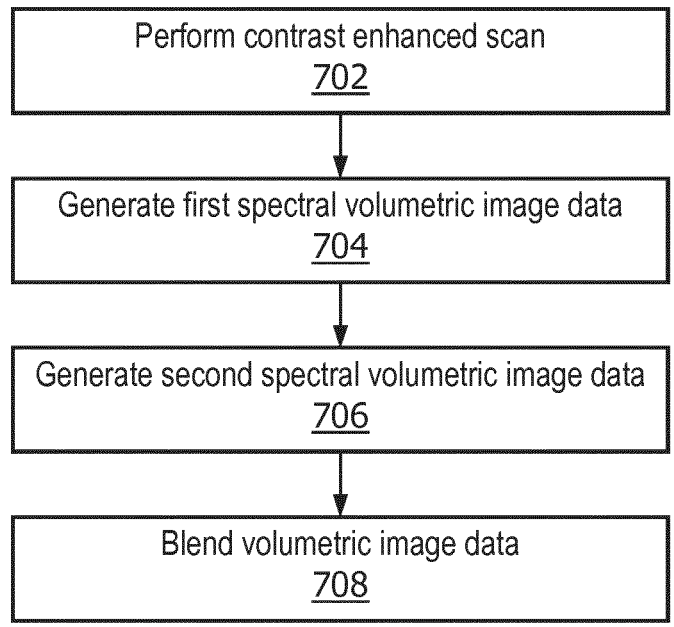
FIG. 7 illustrates another example method in accordance with an embodiment herein.

FIG. 7 illustrates an example method in accordance with an embodiment(s) described herein.

It is to be appreciated that the ordering of the acts in the method is not limiting. As such, other orderings are contemplated herein. In addition, one or more acts may be omitted and/or one or more additional acts may be included.

At 702, a contrast enhanced scan is performed.

At 704, first spectral volumetric image data emphasizing a first material of interest is reconstructed.

At 706, second spectral volumetric image data emphasizing a second material of interest is reconstructed.

At 708, the first spectral volumetric image data and the second spectral volumetric image data are blended together to produce blended volumetric image data, as described herein and/or otherwise.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium, which is not computer readable storage medium.

Figure 8:
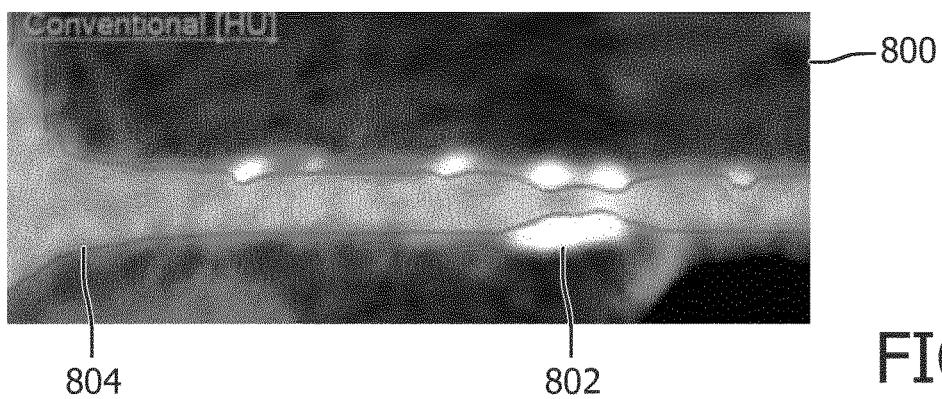
FIG. 8 shows a conventional (120 kVp) image.
Figure 9:
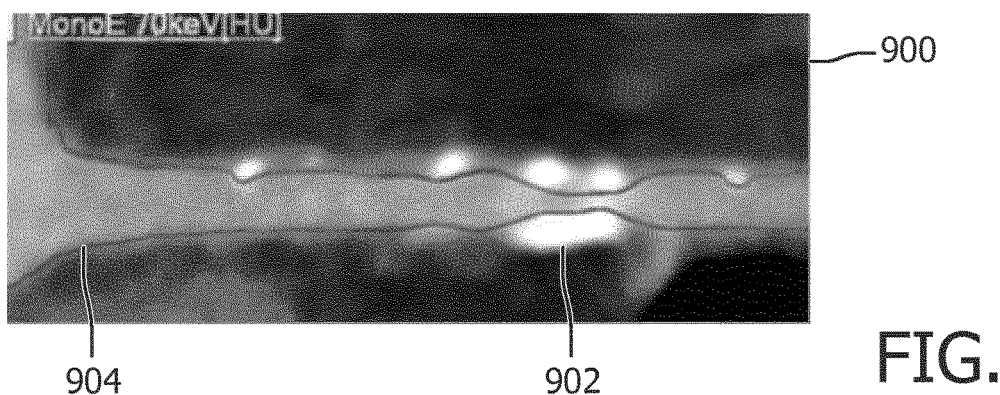
FIG. 9 shows a virtual 70 keV mono-energetic image.
Figure 10:
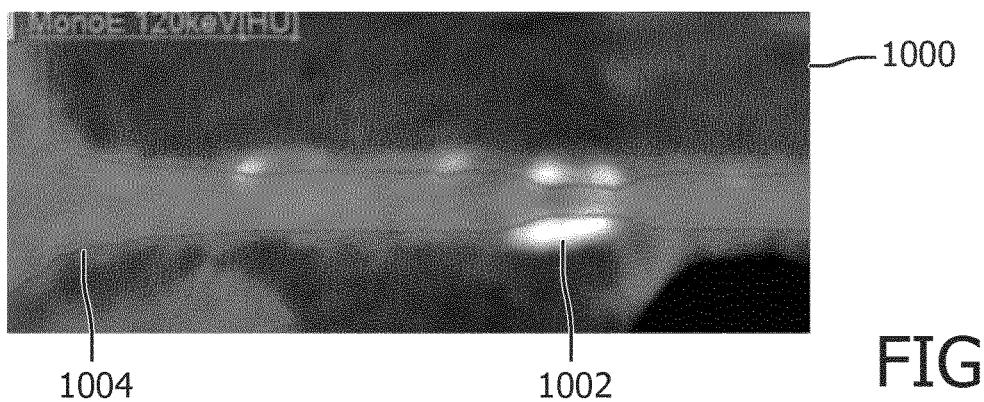
FIG. 10 shows a virtual 120 keV mono-energetic image.
Figure 11:
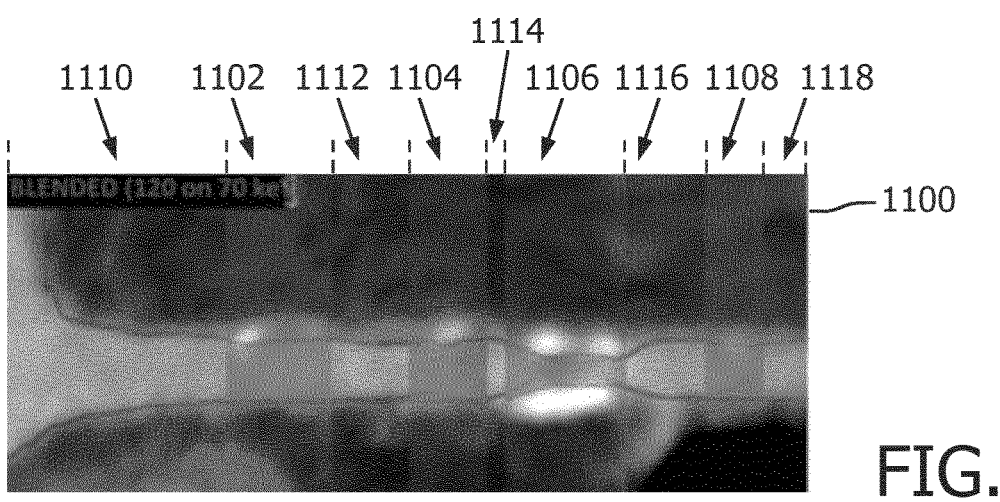
FIG. 11 shows a blended 70/120 keV image.

FIGS. 8-11 illustrate a non-limiting example of the approach described herein. FIG. 8 shows a conventional (non-spectral) 120 kVp image 800, FIG. 9 shows a virtual 70 keV mono-energetic image 900, FIG. 10 shows a virtual 120 keV mono-energetic image 1000, and FIG. 11 shows a blended image 1100 constructed from the virtual 70 keV mono-energetic image of FIG. 9 and the virtual 120 keV mono-energetic image of FIG. 10.

As discussed herein, the higher keV image 1000 will have less blooming artifact 1002 (e.g., smaller diameter) relative to a blooming artifact 802 of the conventional image 800 and a blooming artifact 902 of the lower keV image 900. Additionally, the lower keV image 900 will have a more accurate vessel lumen segmentation 904 relative to a vessel lumen segmentation 804 of the conventional image 800 and a vessel lumen segmentation 1004 of the higher keV image 1000 due to increased contrast agent/soft tissue contrast.

The blended image 1100, in this example, includes portions of the higher keV image 1000 and portions of the lower keV image 900. In particular, regions 1102, 1104, 1106 and 1108, which include pixels representing calcium, are constructed from the higher keV image 1000, which has lower blooming artifact, and regions 1110, 1112, 1114, 1116 and 1118, which include pixels representing vessel lumen and no calcium, are constructed from the lower keV image 900, which has a more accurate vessel lumen segmentation.

It is to be understood that this example is not limiting. The concept of blending can also be applied to conventional and higher keV image to take advantage of reduced blooming of the calcium from the higher keV image. Generally, mono energetic images, for at least a contrast enhanced plaque study, offer trade-offs between contrast agent/soft tissue contrast and blooming artifact. By selectively blending portions of different the mono energetic images, a blended image can be contructed with both enhanced contrast agent/soft tissue contrast and decreased blooming artifact, which is more accurate than a non-spectral image or any of individual mono energetic images.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An imaging system, comprising:
a memory that stores a plurality of instructions; and
processor circuitry that couples to the memory and is configured to execute the plurality of instructions to:
reconstruct the projection data with reconstruction algorithms and generate at least first spectral volumetric image data corresponding to a first basis material content and second spectral volumetric image data corresponding to a second basis material content;
create a first map for the first spectral volumetric image data that identifies which voxels contain mostly the first basis material content and which voxels do not;
create a second map for the second spectral volumetric image data that identifies which voxels contain mostly the second basis material content and which voxels do not;
blend the first spectral volumetric image data and the second spectral volumetric image data with at least one blending algorithm; and
based on the first and second spectral volumetric image data produce blended volumetric image data with voxels with values corresponding to a weighted combination of voxels of first spectral volumetric image data that contain mostly the first basis material content as identified by the first map and values from the second spectral volumetric image data, and voxels with values corresponding to a weighted combination of voxels of second spectral volumetric image data that contain mostly the second basis material content as identified by the second map and values from the first spectral volumetric image data.

2. The system of claim 1, wherein the processor circuitry is further configured to reconstruct the projection data and generate non-spectral volumetric image data, and to blend the non-spectral volumetric image data with at least one of the first spectral volumetric image data or the second spectral volumetric image data to produce the blended volumetric image data with voxels with values from only the non-spectral volumetric image data and voxels with values corresponding to a weighted combination of voxels of the first spectral volumetric image data that contain mostly the first basis material content as identified by the first map or voxels of the second spectral volumetric image data that contain mostly second basis material content as identified by the second map and values of voxels from the non-spectral volumetric image data.

3. The system of claim 1, wherein the processor circuitry is further configured to reconstruct the projection data, generate non-spectral volumetric image data and blend the non-spectral volumetric image data with the first spectral volumetric image data and the second spectral volumetric image data to produce the blended volumetric image data with (a) voxels with values from only the non-spectral volumetric image data, (b) voxels with values corresponding to a weighted combination of voxels of the first spectral volumetric image data that contain mostly the first basis material content as identified by the first map and values of voxels from the non-spectral volumetric image data, and (c) voxels with values corresponding to a weighted combination of voxels of the second spectral volumetric image data that contain mostly second basis material content as identified by the second map and values of voxels from the non-spectral volumetric image data.

4. The system of claim 1, wherein the processor circuitry is configured to blend by combining voxels values on a voxel by voxel basis.

5. The system of claim 4, wherein the processor circuitry is configured to blend voxels at a same location by up-weighting a value of a voxel of volumetric image data emphasizing material content of interest and down-weighting a value of a voxel of other material.

6. The system of claim 5, wherein each voxel contributes to a final voxel value.

7. The system of claim 5, wherein only one voxel contributes to a final voxel value.

8. The system of claim 5, wherein the processor circuitry is configured to smooth values of voxels there between.

9. The system of claim 5, wherein the processor circuitry is configured to smooth values of voxels adjacent thereto.

10. The system of claim 1, wherein the first basis material content is calcium and the second basis material content is iodine, and the volumetric image data is blended to reduce blooming artifact while maintaining contrast between a contrast agent and soft tissue.

11. A method, comprising:
performing a contrast enhanced scan, which produces projection data;
reconstructing the projection data to produce non-spectral volumetric image data;
reconstructing the projection data to produce first spectral volumetric image data for a first basis material;
reconstructing the projection data to produce second spectral volumetric image data for a second basis material; and
blending at least two of the non-spectral volumetric image data, the first spectral volumetric image data, and the second spectral volumetric image data, producing blended volumetric image data, wherein the blended volumetric image data includes voxels with values only from the non-spectral volumetric image data and only from the first spectral volumetric image data, voxels with values only from the non-spectral volumetric image data and only from the second spectral volumetric image data, or only from the first spectral volumetric image data and only from the second spectral volumetric image data.

12. The method of claim 11, further comprising:
generating for the first or second spectral volumetric image data a first or second mapping indicating, on a voxel basis, voxels which primarily represent a first or second basis material.

13. The method of claim 12, further comprising:
blending a voxel of the first or second spectral volumetric image data and a corresponding voxel of the non-spectral volumetric image data with the first or second mapping using a greater contribution of the voxel of the first or second spectral volumetric image data relative to the voxel of the non-spectral volumetric image data for a voxel that primarily represents the first or second basis material.

14. The method of claim 12, further comprising:
blending a voxel of the first or second spectral volumetric image data and a corresponding voxel of the second or first spectral volumetric image data using a greater contribution of the voxel of the first or second spectral volumetric image data relative to the voxel of the second or first spectral volumetric image data for a voxel that primarily represents the first or second basis material.

15. The method of claim 11, further comprising:
weighting voxels of the non-spectral volumetric image data that do not include any of the first and second basis materials with a value of one and corresponding voxels of the first and second spectral volumetric image data with values of zero for the blending.

16. A non-transitory computer readable medium encoded with computer executable instructions, which, when executed by a processor of a computer, cause the processor to:
receive projection data generated from a contrast enhanced scan;
reconstruct the projection data to produce non-spectral volumetric image data;
reconstruct the projection data to produce first spectral volumetric image data for a first basis material;
reconstruct the projection data to produce second spectral volumetric image data for a second basis material; and
blend at least two of the non-spectral volumetric image data, the first spectral volumetric image data, and the second spectral volumetric image data, producing blended volumetric image data, wherein the blended volumetric image data includes voxels with values only from the non-spectral volumetric image data and only from the first spectral volumetric image data, voxels with values only from the non-spectral volumetric image data and only from the second spectral volumetric image data, or only from the first spectral volumetric image data and only from the second spectral volumetric image data.

17. The non-transitory computer readable medium of claim 16, wherein the computer executable instructions, when executed by the processor, further cause the processor to:
for voxels containing mostly the first basis material, up-weight the first spectral volumetric image data and down-weight the non-spectral volumetric image data.

18. The non-transitory computer readable medium of claim 16, wherein the computer executable instructions, when executed by the processor, further cause the processor to:
for voxels containing mostly the second basis material, up-weight the second spectral volumetric image data and down-weight the non-spectral volumetric image data.

19. The non-transitory computer readable medium of claim 16, wherein the computer executable instructions, when executed by the processor, further cause the processor to:
blend other voxels for a smooth transition.

20. The non-transitory computer readable medium of claim 16, wherein the computer executable instructions, when executed by the processor, further cause the processor to:
blend voxels using a location-specific adaptation.

* * * * *